United States Patent
Maskrot et al.

(10) Patent No.: US 11,768,165 B2
(45) Date of Patent: Sep. 26, 2023

(54) METHOD FOR CHARACTERISING AND MONITORING THE HOMOGENEITY OF METAL PARTS MANUFACTURED BY LASER SINTERING

(71) Applicant: COMMISSARIAT À L'ÉNERGIE ATOMIQUE ET AUX ÉNERGIES ALTERNATIVES, Paris (FR)

(72) Inventors: Hicham Maskrot, Montlhery (FR); Alexandre Semerok, Palaiseau (FR)

(73) Assignee: COMMISSARIAT Á L'ÉNERGIE ATOMIQUE ET AUX ÉNERGIES ALTERNATIVES, Paris (FR)

( * ) Notice: Subject to any disclaimer, the term of this patent is extended or adjusted under 35 U.S.C. 154(b) by 152 days.

(21) Appl. No.: 16/954,043

(22) PCT Filed: Dec. 18, 2018

(86) PCT No.: PCT/FR2018/053356
§ 371 (c)(1),
(2) Date: Oct. 3, 2020

(87) PCT Pub. No.: WO2019/122672
PCT Pub. Date: Jun. 27, 2019

(65) Prior Publication Data
US 2021/0096090 A1    Apr. 1, 2021

(30) Foreign Application Priority Data
Dec. 19, 2017 (FR) ...................... 1762519

(51) Int. Cl.
*G01N 25/18* (2006.01)
*G01N 33/20* (2019.01)

(52) U.S. Cl.
CPC ............ *G01N 25/18* (2013.01); *G01N 33/20* (2013.01)

(58) Field of Classification Search
CPC ............................... G01N 25/18; G01N 33/20
See application file for complete search history.

(56) References Cited

U.S. PATENT DOCUMENTS

| | | | | |
|---|---|---|---|---|
| 4,875,175 A | * | 10/1989 | Egee | G01N 21/171 702/30 |
| 6,073,464 A | * | 6/2000 | Boher | B24B 37/013 65/117 |
| 6,657,708 B1 | * | 12/2003 | Drevilion | G01N 21/65 356/73 |

(Continued)

FOREIGN PATENT DOCUMENTS

FR    3007523 A1    12/2014

OTHER PUBLICATIONS

Machine translation of FR3007523 A1 (Published on Dec. 6, 2014).*

(Continued)

*Primary Examiner* — Alesa Allgood
*Assistant Examiner* — Sangkyung Lee
(74) *Attorney, Agent, or Firm* — Pearne & Gordon LLP

(57) ABSTRACT

A non-destructive method for characterizing and monitoring the homogeneity of metal parts which are being manufactured by sintering and comprise several distinct zones. Laser radiation is applied successively to each zone and each sintered zone is analyzed simultaneously in real time by lock-in laser-active radiometry.

5 Claims, 5 Drawing Sheets

(56) References Cited

U.S. PATENT DOCUMENTS

| | | | |
|---|---|---|---|
| 7,995,195 B2* | 8/2011 | Feichtinger | G01K 11/125 |
| | | | 356/43 |
| 2002/0011852 A1* | 1/2002 | Mandelis | G01R 31/311 |
| | | | 324/750.02 |

OTHER PUBLICATIONS

Semerok, Alexandre et al. "Lock-in thermography for characterization of nuclear materials" In: EPJ Nuclear Sciences & Technologies, Jan. 1, 2016, vol. 2, pp. 20.
Escola, Facundo Zaldivar et al. "Characterization of Sintered Mixed Oxides by Photothermal Microscopy" In: International Journal of Thermophysics, Jan. 11, 2016, vol. 37, No. 2, pp. 1-18.
Tolev, J. et al. "Laser photothermal non-destructive inspection method for hairline crack detection in unsintered automotive parts: A statistical approach" Jun. 1, 2010, vol. 43, No. 4, pp. 283-296.
Search Report for French Application No. FR1762519 dated Sep. 19, 2018.
International Search Report for PCT/FR2018/053356 dated Mar. 28, 2019.
Written Opinion for PCT/FR2018/053356 dated Mar. 28, 2019.

\* cited by examiner

METHOD FOR CHARACTERISING AND MONITORING THE HOMOGENEITY OF METAL PARTS MANUFACTURED BY LASER SINTERING

CROSS-REFERENCE TO RELATED APPLICATIONS

This is a National Stage of PCT international application PCT/FR2018/053356, filed on Dec. 18, 2018, which claims the priority of French Patent Application No. 1762519, filed Dec. 19, 2017, both of which are incorporated herein by reference in their entirety.

TECHNICAL FIELD

The invention is concerned with the field of manufacturing metal parts by sintering and more specifically relates to a non-destructive method for characterising and monitoring homogeneity of metal parts when manufactured.

The invention also relates to a device for implementing the method according to the invention.

STATE OF PRIOR ART

In many industrial sectors such as mechanical engineering, electronics, aeronautics, metallurgy, or non-destructive monitoring, precise knowledge of the homogeneity and thermal properties of a material is valuable information. This information is obtained within the scope of a quality monitoring generally carried out after manufacturing parts.

Several techniques are known to carry out this monitoring such as for example radiology, ultrasonic monitoring, modulated photothermal radiometry.

Examining the structure or internal state of an object by radiography consists in passing an electromagnetic radiation with a very short wavelength (X or γ rays) therethrough and collecting intensity modulations of the beam as an image on an appropriate receiver or, in most cases, a film.

According to the same principle, images can be obtained by using other particles than photons, and thus, techniques such as neutron radiography can be implemented.

Radiography is a non-destructive monitoring method which consists in obtaining an image of the material density of an object through which an X or gamma electromagnetic radiation passes. The principle of the method is based on differential absorption of the medium as a function of the atomic number of atoms making it up and density. Any lack of material will induce a lower absorption and thus, locally, a stronger optical density on the film or a higher grey level in the case of digital images. In industrial radiology, X-rays are produced, most often by an X-ray tube, or a particle accelerator for high energy applications. Gamma radiation sources used industrially are iridium 192, cobalt 60 and selenium 75. Radiography is a technique which enables lacks of material of the volume of the object monitored on a two-dimension image to be viewed.

Neutron radiography is a nuclear measurement technique (non-destructive monitoring) the principle of which is similar to that of X-ray radiography but which employs neutrons as a radiation source. A transmission image is produced by interposing the inspected object between a neutron source (often from a reactor) and a neutron detection system. Neutron flux attenuation is more or less pronounced as a function of the nature of the material found, thereby giving rise to contrast differences allowing analysis of the object content.

The ultrasonic monitoring principle consists in emitting and propagating an ultrasonic wave in the part to be inspected. And then, the wave is collected and analysed at the end of its interaction with the material. Based on this very general principle, there are many specific techniques, depending on whether monitoring is carried out in transmission or reflection, or the emission and reception devices are the same or not, and finally, depending on the type and tilt of the ultrasonic waves used, etc. The most widespread monitoring mode, called reflection mode, is comparable to medical ultrasonography. The transmitter and receiver (being the same or not) are positioned on the same side of the part. The receiver collects echos produced by reflection or diffraction on obstacles met by the wave, such as defects, interfaces between materials or the surface of the part. The transmitter and receiver devices, called "ultrasonic translators", are generally based on the piezoelectric effect. The main element, the transducer, consists of a piezoelectric chip converting an electric signal into mechanical vibration and reversely.

Methods for determining thermophysical parameters of a body from the analysis of thermal waves emitted by the body are also known. These methods are distinguished by:

- the heating type (time, space),
- the location of the heat source and the detector on the diagnosis object,
- the location of the heat source and the measurement point, with respect to each other (in the centre of the beam or nearby),
- the number of measurement points. There are already many theoretical methods for different characterisation types.

By associating the temperature measurement to heating modelling, it is possible to determine, under some conditions, thermal properties of the surface. This technique can be employed more specifically, to measure non-destructively and remotely, properties of a layer or coating on a known substrate. In the field of non-destructive active thermal monitoring, four different methods listed and described hereinafter can be distinguished:

- pulsed method;
- continuous heating method;
- periodical pulsed method;
- synchronous detection modulated photothermal radiometry method, also called "Lock-in".

In the case of pulsed heating, the material is subjected to a single pulse from the heat source (for example, a pulsed laser), with known energy parameters. By using the cooling curve of the material, the desired thermophysical properties searched for are then obtained by reverse resolution of heat transfer equation. This technique enables a solution to be obtained from data of a relatively short measurement.

Many pulsed methods have been developed to characterise homogeneous materials and coated with one or more layers. The most used method is a measurement of one of the thermal phenomena in the front face of the sample, that is the heated surface. Most studies are dedicated to measurements in the centre of the laser beam, but temperature variation can be followed in a side direction. One of the applications is the defect characterisation. Thermal properties attempted to be determined are diffusivity, effusivity, thermal conductivity or combinations of these properties.

The second category of active pyrometry methods is based on a continuous heating of the surface. As for the first method, the main parameter is surface temperature and its deviation with respect to reference materials called thermal contrast. The advantage of this method, as in the first case, is its quickness but, unlike the low cooling temperature signal of the pulsed heating, continuous heating enables measurements to be made with higher and thus more accurate temperatures. However, heating leads to the risk of overheating the material and, consequently, modifying properties thereof.

As previously indicated, stepwise heating enables characteristics of the layer to be determined by comparing the model estimated from experience.

Repeated pulsed heating makes it possible to overcome drawbacks of both previous methods. The temperature is maintained at a sufficient level for measurements, while reducing the risk of overheating the surface.

One problem of the above methods comes from the fact that they cannot be implemented when manufacturing the part because the emissivity of the material is generally not known, thus leading to inaccurate results, or even incorrect measurements of the temperature. In addition, to determine thermal properties from temperature measurements, heating flow absorbed by the surface and, thus, laser power as well as absorption coefficient have to be known.

The purpose of the invention is to perform defect detection in real time on a part manufactured by sintering without knowing a priori heating flow absorbed by the surface and, thus, laser power as well as absorption coefficient.

DISCLOSURE OF THE INVENTION

This purpose is achieved by means of a non-destructive method for characterising and monitoring the homogeneity of metal parts including several distinct zones manufactured by sintering, wherein a laser radiation is successively applied on each zone and an analysis of each sintered zone is simultaneously performed in real time by synchronous detection active laser radiometry.

Preferentially, the laser radiation is successively applied on successive sub-zones of each zone so as to use a low-power laser radiation, the size of said sub-zones having a regular shape on which the laser radiation is applied row by row so as to form an image of the sintered zone in real time.

According to another characteristic of the invention, a frequency modulated heating generating at each frequency a single thermal wave is applied on each zone, and for each frequency, the phase shift between the luminous signal of the laser applied to the part and the thermal signal emitted by the part is measured in real time.

According to the invention, the thickness L (µm) and thermal diffusivity D (m²/s) of each zone are determined by the following formulae:

$$L = \frac{r_0}{\zeta_\varphi} \ln \frac{\pi}{|\varphi_{min}|} \quad (1)$$

$$D = \frac{1}{\zeta_f} f_{min} L r_0 \quad (2)$$

where $r_0$ is the laser beam radius at 1/e intensity; $\varphi_{min}$ and $f_{min}$ represent the minimum phase shift and laser beam rate respectively; $\zeta_\varphi$ and $\zeta_f$ represent known coefficients which depend on the minimum phase shift $\varphi_{min}$ and ratio $r_0/L$ respectively.

The method according to the invention is implemented by a device including a laser source adapted to apply successively on each zone of the part monitored a laser radiation, an infrared radiation detector adapted to sense and measure in real time the thermal radiation emitted by each zone of said part, a synchronous detector for detecting phase shift between the luminous signal of the laser radiation and the thermal signal of the infrared radiation emitted by each zone of said part.

The laser source of the device according to the invention is configured to apply on each zone a modulated heating generating at each frequency a single thermal wave, and the synchronous detector is configured to measure, for each frequency, the phase shift between the luminous signal of the laser applied to the part and the thermal signal emitted by the part.

BRIEF DESCRIPTION OF THE DRAWINGS

Further characteristics and advantages of the invention will appear from the description that follows, taken by way of non-limiting example, with reference to the appended figures in which.

DETAILED DISCLOSURE OF PARTICULAR EMBODIMENTS

The invention will be described in an application for manufacturing and characterising metal parts used in nuclear industry in real time.

Figure 1:
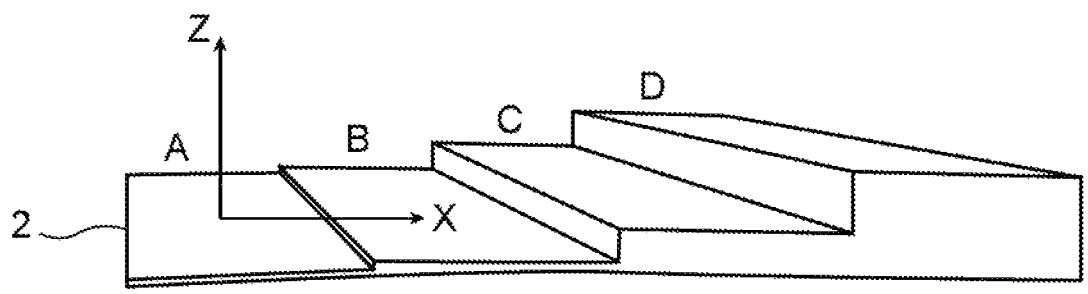
FIG. 1 schematically illustrates a sample of a metal part obtained by the additive manufacturing method using the method according to the invention.
Figure 2:
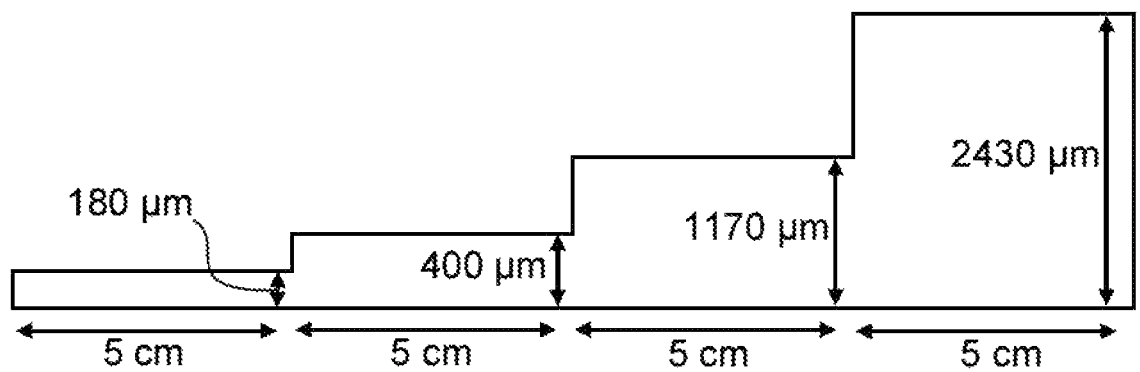
FIG. 2 illustrates dimensions of different zones of the sample of FIG. 1.
Figure 3:
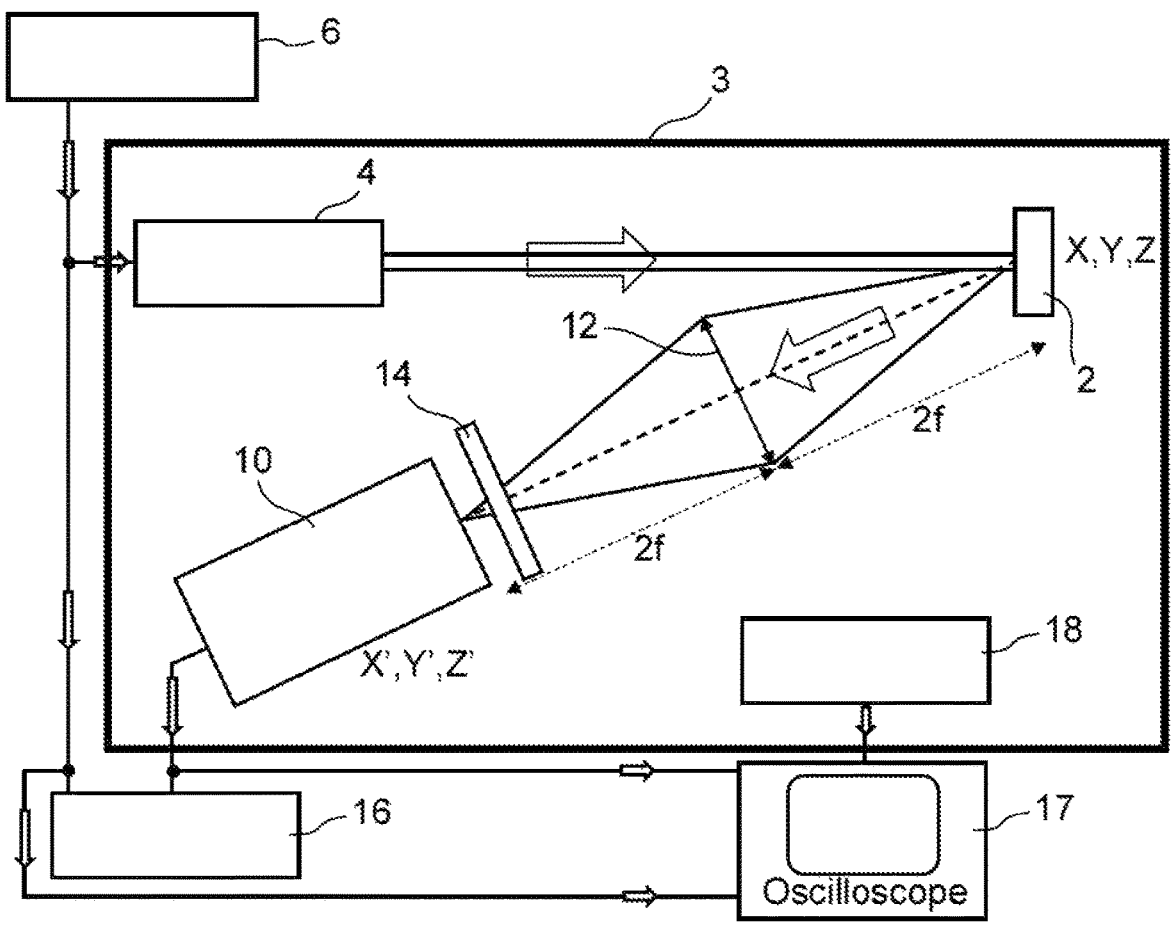
FIG. 3 schematically illustrates a device for characterising and monitoring homogeneity of metal parts according to the invention.

By way of illustrating example, the method will be applied to a metal sample 2 having (side) dimensions of 20 mm×20 mm and thicknesses 180 µm to 2430 µm obtained by the additive manufacturing method using 316 L stainless steel powder illustrated by FIGS. 1 and 2.

Sample 2 includes four distinct zones A, B, C and D having respectively as thicknesses 180±20 µm (zone A), 400±20 µm (zone B), 1170±20 µm (zone C), 2430±20 µm (zone D). The surface roughness is ±20 µm. The thermal diffusivity of this sample of 316 L stainless steel is D=0.039±0.004 cm²/s [4] for room temperature.

Zones A and B have been examined by the method according to the invention during manufacturing by means of device 3. The latter includes a fibre laser source 4 with a wavelength of 1080 nm to heat sample 2 with a mean power tunable from 0 to 50 W. This mean power can be modulated.

The radius $r_0$ of the beam collimated at sample 2 is equal to 1740 μm (radius at 1/e intensity). The laser power (amplitude and rate) is managed by a function generator 6. The output of the generator 6 (output impedance: 50Ω) is separated into two ways, one for laser operation (input impedance: 50Ω) and the other for use as the reference signal of a synchronous detection amplifier (input impedance: 1 MΩ).

The function generator 6 can produce a continuous signal or a sinusoidal, rectangular or triangular modulated signal, having variable amplitude and frequency. Laser source 4 delivers up to 50 W continuous output power and up to 25 W (mean power) sinusoidal output power, with a beam quality which is close to the diffraction limit with $M^2<1.1$. Laser characteristics are set out in the table below.

| Characteristics of fibre laser source 4. | | |
|---|---|---|
| Operating mode | | Continuous, modulated |
| Central wavelength | nm | 1080 |
| Beam shape | | Gaussian, collimated |
| Beam quality ($M^2$) | | 1.1 |
| Beam diameter at 1/e | μm | 1740 ± 30 |
| Maximum power (peak or cw) | W | 50 |
| Modulation rate | Hz | ≤5 kHz |
| Maximum voltage of the generator | V | 5 |
| Dimensions | mm | 448 × 451 × 132 |

Laser source 4 has a low power infrared beam to indicate the beam direction and facilitate optical adjustment of the samples before experimental tests. The mean power of the sinusoidal mode laser signal does not depend much on the rate applied. The variation in the laser signal power remains low, such that it can be considered that the mean heating temperature remains the same for rates from 1 Hz to 1 kHz. This enables the same thermal properties to be kept for the entire duration of the measurements with different rates, which ensures better accuracy in the measurements.

Device 3 further includes an IR detector 10 to measure the thermal radiation of the sample 2 when the same is lit by laser source 4. The wanted spectral range of the IR detector 10 extends from 1.5 μm to 11 μm. A convex lens 12 of ZnSe is used to image the heated zone retained on a surface of the detector with a radius of 800 μm. A germanium filter 14, only transmitting wavelengths between 2 μm and 14 μm, has been placed in front of the IR detector 10, in order to prevent diffuse reflection from the laser signal from disturbing detection (because the detector has a residual sensitivity at the wavelength of 1 μm).

A synchronous detection amplifier 16 is used to determine phase shift between the luminous signal of the laser and the thermal signal as a function of the laser signal frequency.

The synchronous detection amplifier 16 is connected to an electronic oscilloscope 17. The laser signal power is controlled by a laser power detector 18 also connected to the electronic oscilloscope 17.

Analysis of the phase shift curve enables some properties of the sample 2 to be determined.

To avoid flybacks into the laser, the surface of the sample is placed with a small angle θ with respect to the plane perpendicular to the incident normal axis. The beam size is then multiplied by cos θ in one direction. θ is chosen low, that is lower than 10° so as to be in the scope of the approximation cos θ~1.

Figure 4:
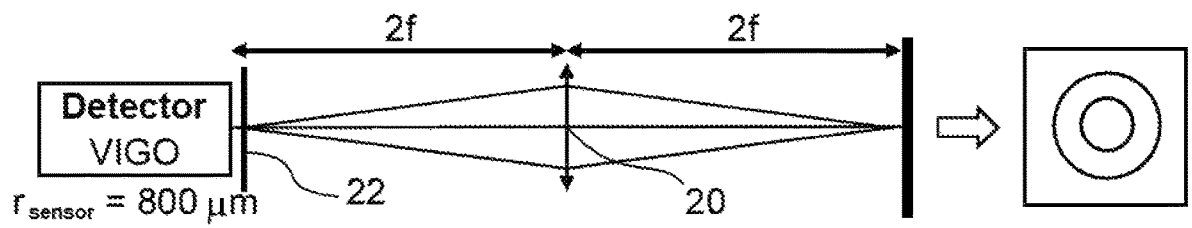
FIG. 4 schematically illustrates an embodiment of the optical system used in the device for characterising and monitoring homogeneity of metal parts according to the invention.

FIG. 4 schematically represents the optical system used in the device 1. This optical system includes a ZnSe lens 20 (transmission spectral range from 0.6 μm to 15 μm) used to focus thermal flux onto the sensitive zone of the IR detector 10 and a Germanium filter 22 (transmission spectral range from 1.8 μm to 23 μm) to cut-off all the wavelengths up to 1.8 μm, thus filtering the laser wavelength.

The ZnSe convex lens 20, with a focal distance of 50 mm and a diameter of 25 mm, makes an image on the IR detector 10 the centre of the zone heated by the laser. The capture surface area of the IR detector has a radius of 800 μm. To only image the central part of the zone heated by the laser beam limited to half its radius, that is $r_{heating}/2=870$ μm, the magnification $r_{sensor}/r_{collected}$ is higher than or equal to 1 and the lens-sample distance is 2f=100 mm.

By way of example of implementation of the method according to the invention, the phase shift curves as a function of the laser signal frequency will be determined for zones A and B of sample 2. The phase shift curves obtained enable the optimum rate to be determined for a better distinction (maximum $\Delta_\varphi$) between zones A and B. All the measurements have been made on the homogeneous side where the steps of the sample are not visible.

Once the optimum rate is determined, the laser beam is moved along axis x and axis z to study homogeneity in the properties of the sample along these axes. Axes have been chosen such that it is possible to change thickness along axis x without changing thickness along axis z.

In use, a zone is heated with the laser source 4, by varying the laser signal frequency from 1 to 200 Hz. The mean power is 11 W (amplitude of the 3V generator). Given that the frequency variation only slightly affects the laser output power, the temperature variation should be limited in order not to affect measurements with the different rates.

Measurements have been made on two zones with different thicknesses, one of 180 μm and the other of 400 μm.

Figure 5:
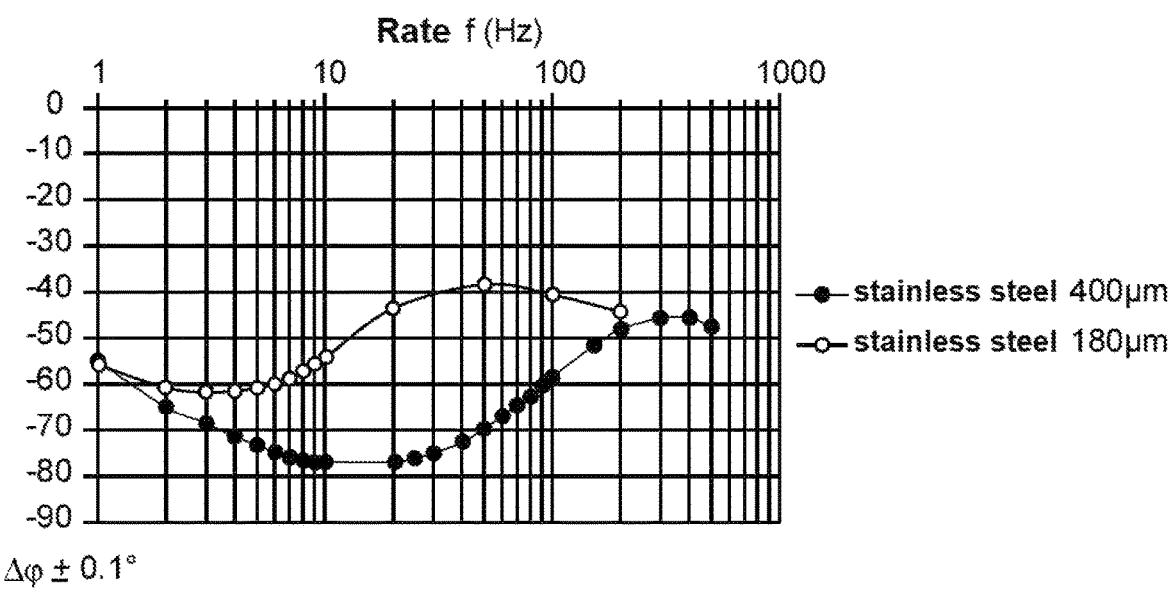
FIG. 5 is a curve illustrating variations of phase shifts measured as a function of the frequency for the sample of FIG. 1 for two different thicknesses.

FIG. 5 represents phase shifts obtained. This curve enables the minimum phase shift $\varphi_{min}$ and the corresponding frequency $f_{min}$ to be determined and, through the following formulae (1) and (2), thickness L (μm) and thermal diffusivity D (m²/s) in tested zones:

$$L = \frac{r_0}{\zeta_\varphi} \ln \frac{\pi}{|\varphi_{min}|} \quad (1)$$

$$D = \frac{1}{\zeta_f} f_{min} \, L r_0 \quad (2)$$

where $r_0$ is the laser beam radius at 1/e intensity; and M are known coefficients which depend on $\varphi_{min}$ and $r_0/L$ ratio respectively.

The measurement results are set out in the following table 1:

| Results of measurements with sample 2. | | |
|---|---|---|
| | $\varphi_{min}$ | $f_{min}$ |
| Thickness L = 180 μm | −77.1 ± 0.1° | 9 Hz |
| Thickness L = 400 μm | −61.7 ± 0.1° | 3 Hz |

From these results and the coefficients $\zeta_\varphi$ and $\zeta_f$ set out below, it is possible to determine the thickness and diffusivity in zones A and B which are set out in the table hereinafter.

$\zeta_\varphi$=1.535±0.005 (180 μm) and 1.53±0.005 (400 μm)
$\zeta_f$=0.534±0.005 (180 μm) and 0.472±0.005 (400 μm)

The thicknesses and thermal diffusivities determined by the modulated photothermal radiometry method for sample 2 are given in the following table 2:

|  | Measured by Lock-in | Reference for T = 400K |
|---|---|---|
| Thickness ∠ (zone A) | 175.3 ± 26 μm | 180 ± 20 μm |
| Thickness ∠ (zone B) | 429.3 ± 30 μm | 400 ± 20 μm |
| D in zone A | 0.051 ± 0.005 cm²/s | 0.047 ± 0.003 cm²/s |
| D in zone B | 0.047 ± 0.005 cm²/s | 0.047 ± 0.003 cm²/s |

These thicknesses determined by the modulated radiometry method properly match with thicknesses measured by a vernier caliper. Thermal diffusivities measured in two different zones of sample 2 are the same. The measurements made enable the sample 2 to be analysed firstly in the direction where there is a thickness change, and secondly, in the direction where there is no visible change, neither in thickness, nor in thermophysical properties.

To that end, the laser radius frequency is fixed, and is equal to that which yields the greatest phase shift deviation by switching from one zone to the other that is about 20 Hz, which enables the different steps to be well highlighted.

Figure 6:
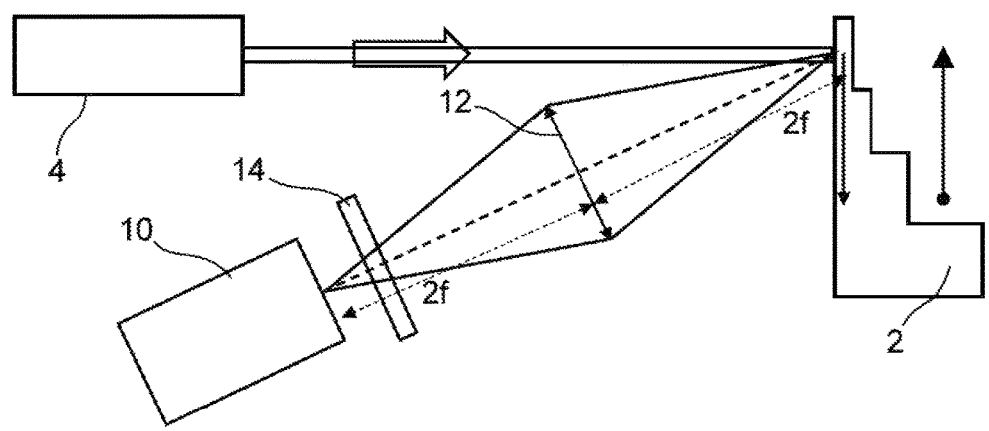
FIG. 6 schematically illustrates a first assembly to measure phase shift as a function of frequency for the metal part of FIG. 4 towards x-axis.

FIG. 6 illustrates the first case of analysing sample 2 in the direction where there is a thickness change.

Figure 7:
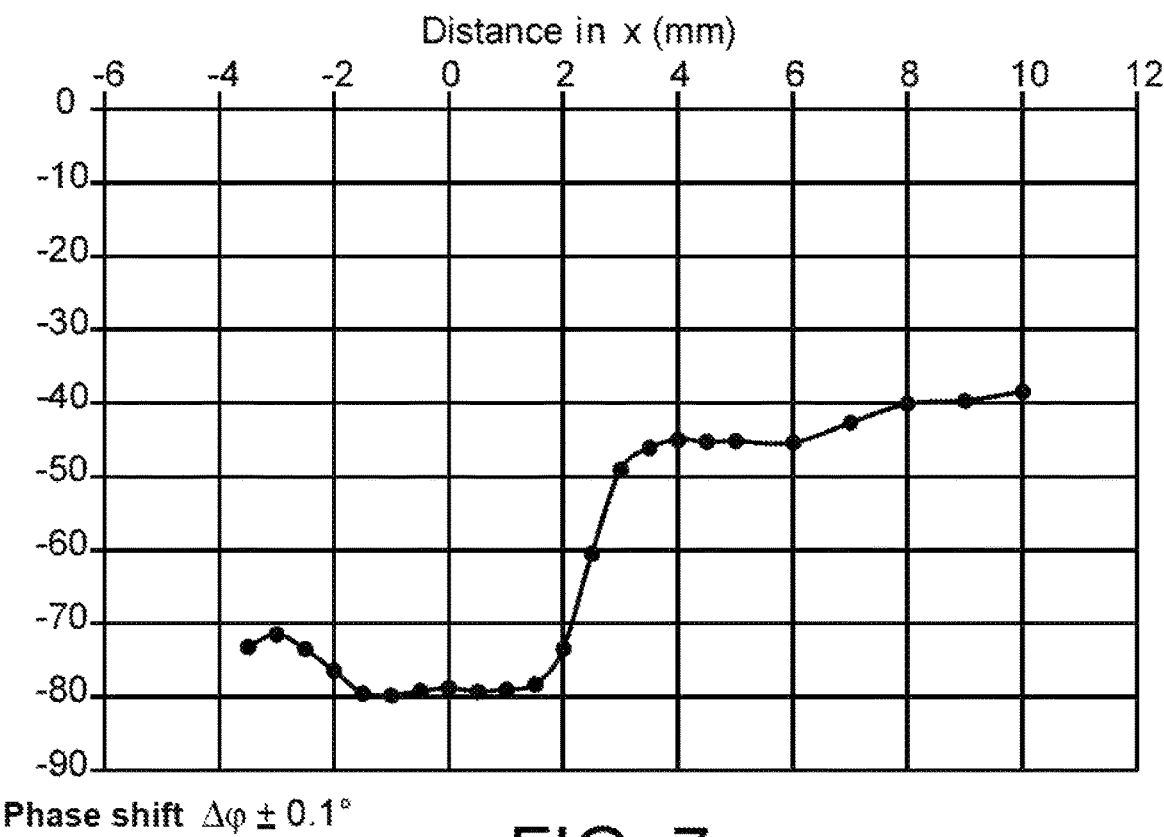
FIG. 7 is a curve illustrating phase shifts measured by the assembly of FIG. 6.

In this case, sample 2 is heated in zone A with a thickness of 180 μm, and then is moved along axis x (to zone B) by a distance of 15 mm with a pitch of 0.5 mm. Phase shifts measured for each position are set out by the curve of FIG. 7.

Both phase shifts represent two thicknesses at two steps located at −80° and −45°. A last step is located at −40°. The chosen frequency is 20 Hz to properly differentiate both steps.

It is observed that the frequency is not adapted to show the difference between the last two steps of 400 and 1170 μm (FIG. 2).

The first part of the curve located for x between −4 and −2 mm shows a defect due to the manufacture of the part.

It is noticed that the method can readily reveal the non-homogeneity (a step) of a monitored part. The spatial resolution is about one millimetre and it is determined by the width of the zone tested by the VIGO detector (1.6 mm). This resolution can be improved by the use of an optical path with a higher resolution.

Figure 8:
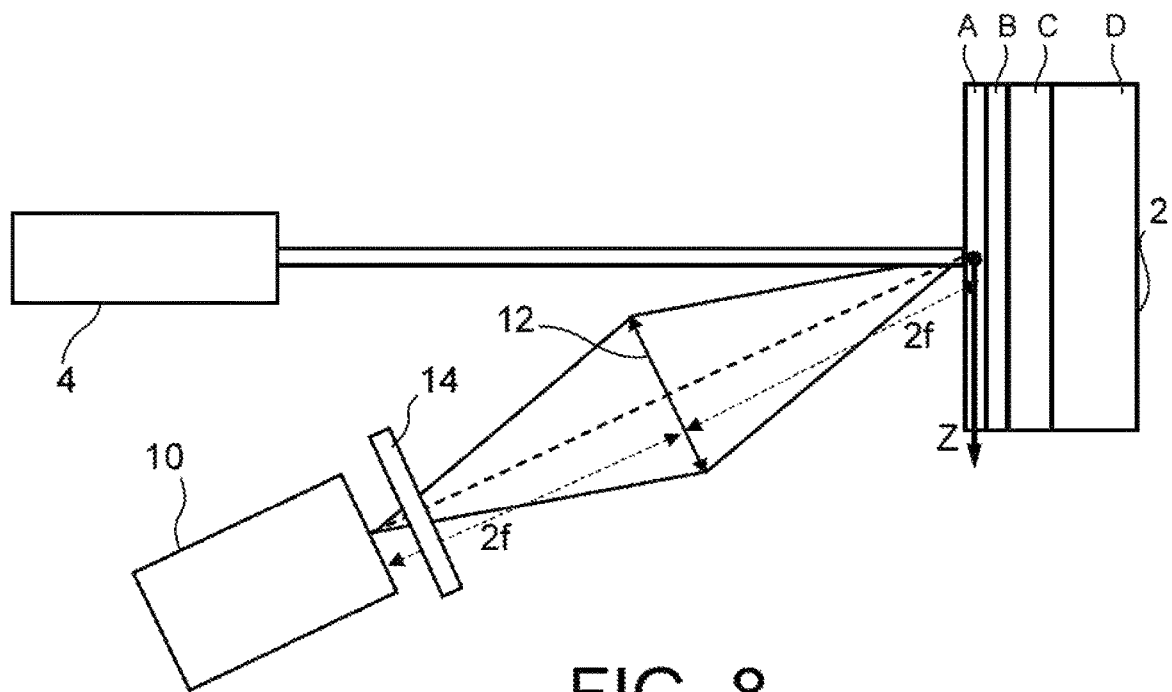
FIG. 8 schematically illustrates a second assembly to measure phase shift as a function of frequency for the metal part of FIG. 4 towards z-axis.

FIG. 8 illustrates the second case of analysing sample 2 in the direction where there is no thickness change.

Figure 9:
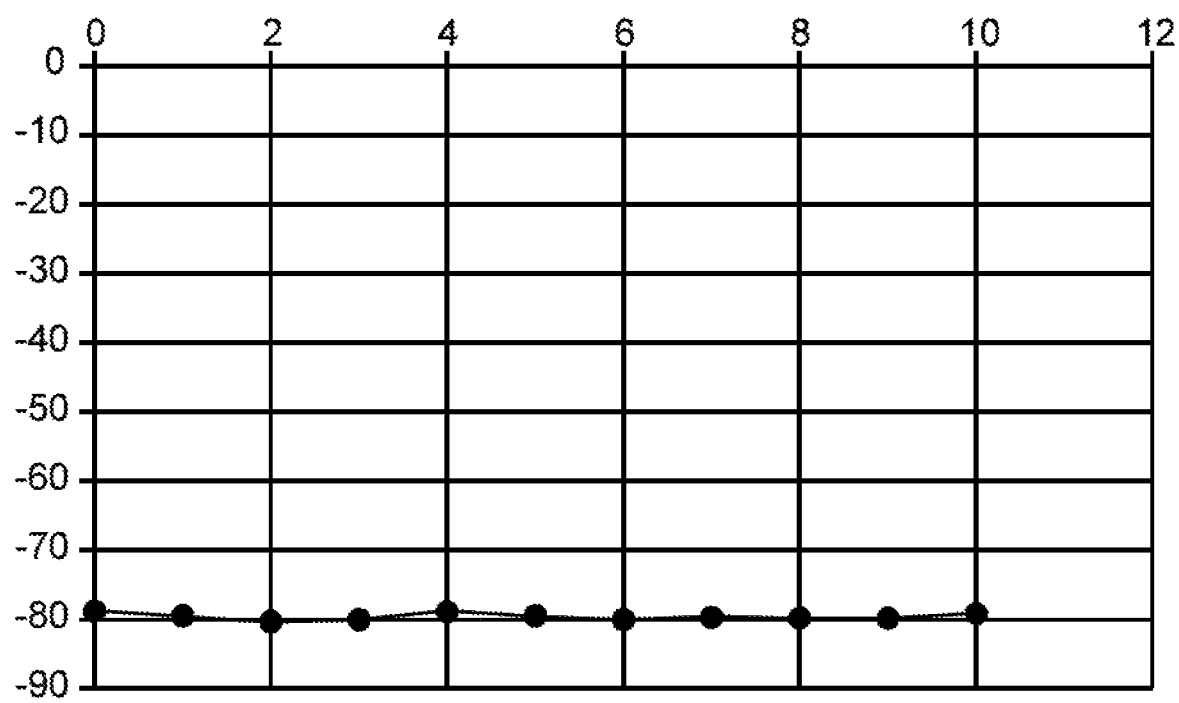
FIG. 9 is a curve illustrating phase shifts measured by the assembly of FIG. 8.

In this case, the sample is heated in zone A with a thickness of 180 μm, and is moved along axis z by a distance of 10 mm with a 0.5 mm pitch. Phase shifts measured for each position are set out by the curve of FIG. 9.

The sample is heated in zone A with a thickness of 180 μm, and then is moved along axis z by a distance of 10 mm with a 0.5 mm pitch.

A phase shift homogeneity is noticed. Indeed, the curve is planar and is located at −80°. That is the reason why the part has no internal or external defect.

The measurements are made in real time, that is, upon manufacturing the part. Thus, it is possible to correct the process of manufacturing parts by sintering in real time.

The invention claimed is:

1. A non-destructive method for characterising and monitoring the homogeneity of a metal part manufactured by sintering including several distinct zones, wherein, upon manufacturing said part:
    a laser radiation is successively applied on each zone and an analysis of each sintered zone is simultaneously made with the laser radiation in real time by synchronous detection active laser radiometry,
    a frequency modulated heating generating at each frequency a single thermal wave is applied on each zone, and for each frequency, the phase shift between the luminous signal of the laser applied to the part and the thermal signal emitted by the part is measured in real time, and,
    the thickness L (μm) and thermal diffusivity D (m²/s) of each zone are determined by the following formulae:

$$L = \frac{r_0}{\zeta_\varphi} \ln \frac{\pi}{|\varphi_{min}|} \quad (1)$$

$$D = \frac{1}{\zeta_f} f_{min} L r_0 \quad (2)$$

where $r_0$ is the laser beam radius at 1/e intensity;
$\varphi_{min}$ and $f_{min}$ represent the minimum phase shift and the laser beam rate respectively;
$\zeta_\varphi$ and $\zeta_f$ represent known coefficients which depend on the minimum phase shift $\varphi_{min}$ and the ratio $r_0/L$ respectively,
wherein a first zone and a second zone have different thicknesses.

2. The method according to claim 1, wherein the laser radiation is successively applied on sub-zones of each zone so as to use a low power laser radiation.

3. The method according to claim 2, wherein the size of said sub-zones has a regular shape on which the laser radiation is applied row by row so as to form an image of the sintered zone in real time.

4. A device for characterising and monitoring the homogeneity of a metal part manufactured by sintering including several distinct zones wherein a first zone and a second zone have different thicknesses, wherein the device includes a laser source adapted to successively apply on each zone a laser radiation upon manufacturing said part and to apply on each zone a frequency modulated heating generating at each frequency a single thermal wave, an infrared radiation detector adapted to sense and measure in real time the thermal radiation emitted by each zone, a synchronous detector for detecting phase shift between the luminous signal of the laser radiation and the thermal signal of the infrared radiation emitted by each zone, and means to determine the thickness L (μm) and thermal diffusivity D (m²/s) of each zone by the following formulae:

$$L = \frac{r_0}{\zeta_\varphi} \ln \frac{90}{|\varphi_{min}|} \quad (1)$$

$$D = \frac{1}{\zeta_f} f_{min} L r_0 \quad (2)$$

where $r_0$ is the laser beam radius at 1/e intensity;
$\varphi_{min}$ and $f_{min}$ represent the minimum phase shift and the laser beam rate respectively;
$\zeta_\varphi$ and $\zeta_f$ represent known coefficients which depend on the minimum phase shift $\varphi_{min}$ and the ratio $r_0/L$ respectively.

5. The method according to claim 1, wherein a side of the first zone is coplanar with a side of the second zone.

* * * * *